United States Patent [19]

Klauck et al.

[11] Patent Number: 5,270,433
[45] Date of Patent: Dec. 14, 1993

[54] POLYURETHANE-BASED UNIVERSAL HOUSEHOLD ADHESIVE

[75] Inventors: Wolfgang Klauck, Meerbusch; Gerhard Gierenz, Solingen; Wolfgang Maier; Rainer Hoefer, both of Duesseldorf; Roland Gruetzmacher, Wuelfrath, all of Fed. Rep. of Germany

[73] Assignee: Henkel Kommanditgesellschaft auf Aktien, Duesseldorf, Fed. Rep. of Germany

[21] Appl. No.: 934,511
[22] PCT Filed: Apr. 2, 1991
[86] PCT No.: PCT/EP91/00630
§ 371 Date: Oct. 9, 1992
§ 102(e) Date: Oct. 9, 1992
[87] PCT Pub. No.: WO91/15529
PCT Pub. Date: Oct. 17, 1991

[30] Foreign Application Priority Data

Apr. 9, 1990 [DE] Fed. Rep. of Germany ....... 4011455

[51] Int. Cl.$^5$ ............................................. C08L 75/04
[52] U.S. Cl. .................... 524/158; 524/236; 524/284; 524/591; 524/714; 524/773; 524/839; 524/840
[58] Field of Search ............... 524/158, 236, 284, 591, 524/714, 773, 839, 840

[56] References Cited

FOREIGN PATENT DOCUMENTS

| | | |
|---|---|---|
| 0197170 | 10/1986 | European Pat. Off. |
| 0354471 | 2/1990 | European Pat. Off. |
| 0369389 | 5/1990 | European Pat. Off. |
| 1595602 | 9/1969 | Fed. Rep. of Germany |
| 1769387 | 10/1971 | Fed. Rep. of Germany |
| 2035732 | 1/1972 | Fed. Rep. of Germany |
| 3630045 | 3/1988 | Fed. Rep. of Germany |
| 3827378 | 2/1990 | Fed. Rep. of Germany |

OTHER PUBLICATIONS

Encyc. of Chem. Tech., Kirk-Othmer, vol. 18, 1982, pp. 633-645.
Angew. Makromol. Chem., D. Dieterich, 1981, pp. 133-165.
Journal of Water Borne Coatings, Zermani, 1984, pp. 2 et seq.
Meth. organischen Chem., Houben-Weyl, vol. E20, Part 131, pp. 1659-1663 and 1671-1681.
Journal of Cellular Plastics, Arendt, 1982, pp. 376-383.
Encyklop. der tech. Chemie, Weinheim/Bergstrasse, 1974, pp. 311-313.

*Primary Examiner*—Maurice J. Welsh
*Attorney, Agent, or Firm*—Ernest G. Szoke; Wayne C. Jaeschke; Real J. Grandmaison

[57] ABSTRACT

The invention relates to the use of a substantially clear and at least largely solventless, aqueous, one-component polyurethane dispersion based on the reaction products of a polyol mixture consisting completely or partly of polypropylene glycol,
a mixture of polyfunctional isocyanates consisting completely or partly of $\alpha,\alpha,\alpha',\alpha'$-tetramethyl xylene diisocyanate (TMXDI),
a functional component capable of salt formation in aqueous solution and
optionally a chain-extending agent as a universal household adhesive and to a process for its production in the absence of inert solvents.

17 Claims, No Drawings

POLYURETHANE-BASED UNIVERSAL HOUSEHOLD ADHESIVE

BACKGROUND OF THE INVENTION

1. Field of the Invention

This invention relates to the use of special, substantially clear, aqueous and at least largely solventless polyurethane dispersions as universal household adhesives and to a process for their production.

Universal household adhesives, also known as multipurpose adhesives, are used for bonding a number of substrates encountered in the home (paper, cardboard, photographs, fabrics, leather, felt, bast, cork, films, metals, such as aluminium and iron, china, ceramics, glass, wood, various plastics, including for example polystyrene foams). The adhesives in question are expected to produce an adequate adhesive effect on these various substrates which differ chemically and physically in their surface structure and which are normally subjected to a special surface treatment before bonding.

Compared with the large variety of classes and types of adhesive used in industry and workshops, there are only a few substances which are capable of meeting the stringent demands imposed on the universality of a multipurpose household adhesive. Among those substances, only polyvinyl acetate and its copolymers are widely used—normally in solution or, for glueing wood, in the form of a dispersion.

The demand for universality represents a particularly difficult selection criterion for an adhesive. Ultimately, it means that the adhesive molecules must show equally high affinity for polar and apolar interfaces. Accordingly, the statement that a certain substance is suitable as an adhesive does not indicate to the expert whether it can also be used as a universal household adhesive.

In addition to the universality requirement, there has also recently been a demand for solventless, physiologically safe, clear, aqueous formulations of neutral odor in the field of universal household adhesives. However, these formulations are intended at the same time to lead to adhesives of which the dried films in turn have a certain resistance to water. In addition, these water-based adhesives are also intended to be able to bond substrates that are difficult to bond, such as plastics. They are also intended to have a long storage life.

This requirement profile could not be fully satisfied either on the basis of the binders hitherto preferred for universal adhesives, namely polyvinyl acetate and vinyl acetate copolymers, or by such alternatives as nitrocellulose. Although polyvinyl acetate can be produced without solvents in the form of aqueous dispersions, the dispersions obtained are not transparent, but milky white. They show good performance properties when used, for example, as wood glue. The acrylates and styrene acrylates widely used as dispersion adhesives are also not known on the market in the form of transparent household adhesives with the properties mentioned.

It is known that specially selected embodiments of the aqueous polyurethane dispersions known for decades are suitable as multipurpose universal adhesives. Polyurethane dispersions consist of adducts of polyfunctional isocyanates (isocyanate component) with polyfunctional OH compounds (polyol component) which contain co-condensed units capable of salt formation in aqueous solution. It has surprisingly been found that polyurethane dispersions in which the polyol component is based on polypropylene glycol and the isocyanate component is based on tetramethyl xylene diisocyanate, are also suitable as universal household adhesives and provide good adhesion values. It has also surprisingly been found that dispersions of the type in question can be produced without using inert solvents.

2. Discussion of Related Art

DE-OS 36 30 045 broadly describes an adhesive based on an aqueous dispersion of polyurethanes containing incorporated carboxylate and/or sulfate groups of which the basic diisocyanate component consists of a mixture of at least two (cyclo)aliphatic diisocyanates. The DE-OS mentions numerous polyols, numerous isocyanate compounds and numerous salt-forming components as modifying agents. It also mentions the chain-extending agents typically used in the field in question. The adhesives are said to be suitable for bonding any substrates.

The broad disclosure of DE 36 30 045 in regard to the polyol component encompasses both polyurethane dispersions, in which polyesters are used as the OH-functional component, and also those in which polyethers are used. However, polyurethane dispersions based on polyurethanes synthesized from OH-functional polyesters are not suitable as universal household adhesives because they undergo hydrolysis in storage and hence do not have the required stability in storage.

Although DE 15 95 602 also mentions polymerization products of propylene oxide, for example, as a possible polyol, there is no reference to the fact that polyols such as these are a suitable basis for polyurethane dispersions for universal household adhesives having the requirement profile mentioned above.

Although universal household adhesives based on polyurethane dispersions which have the stated requirement profile are already known from DE 38 27 378, the dispersions in question are not dispersions in which the polyurethanes are formed by reaction of polypropylene glycol with isocyanates.

Although polymerization products of propylene oxide are mentioned among many other polyethers in DE 38 27 378 and in the corresponding EP 354 471, they are only mentioned as an addition to the described polyol mixture consisting of polytetrahydrofuran. At the same time, it is pointed out in both patents that polyurethane dispersions based on polyethylene oxide and/or polypropylene oxide as the OH-functional component are also unsuitable as multipurpose adhesives because they show poor adhesion to plastic surfaces and, accordingly, do not satisfy the universality requirement. This is consistent with the statement in DE-OS 17 69 387 that polyether diols which have been prepared from oxides, such as ethylene oxide or propylene oxide, are unsuitable as polyol component for the production of polyurethane dispersions intended for the bonding of plasticized PVC plastics.

Among many other suitable isocyanates, EP 354 471 also mentions tetramethyl xylene diisocyanate, although there is no reference to the fact that the combination of this isocyanate with a polyol component based on polypropylene glycol leads to polyurethane dispersions which, when used as multipurpose adhesives, do show good adhesion, for example to plastic surfaces. In addition, there is no reference to the fact that, where this combination is used, the dispersion can be prepared without inert solvents. Instead, the acetone process is preferred in both the cited patents.

Accordingly, the problem addressed by the present invention was to show that special, aqueous, transparent polyurethane dispersions based on a polyol component which, in turn, is based on polypropylene glycol satisfy the complex and partly conflicting requirements mentioned above in regard to universal household adhesives. These requirements also include very good stability to hydrolysis and high adhesive strength. The invention also sought to provide a process by which it would be possible, in contrast to the prior art, to produce polyurethane dispersions suitable as domestic multipurpose adhesives without having to use inert solvents, so that the dispersions could even be produced without any residual solvent content whatever.

DESCRIPTION OF THE INVENTION

Other than in the operating examples, or where otherwise indicated, all number expressing quantities of ingredients or reaction conditions used herein are to be understood as modified in all instances by the term "about."

The present invention relates to the use of a substantially clear and at least largely solventless, aqueous, one-component polyurethane dispersion based on the reaction products of a polyol mixture consisting completely or partly of polypropylene glycol, a mixture of polyfunctional isocyanates consisting completely or partly of $\alpha,\alpha,\alpha',\alpha'$-tetramethyl xylene diisocyanate (TMXDI), a functional component capable of salt formation in aqueous solution and optionally a chain-extending agent as a universal household adhesive.

The present invention also relates to a process for the production of the polyurethane dispersions suitable as universal household adhesives.

The polyurethanes forming the basis of the polyurethane dispersions used in accordance with the invention are based on a polyol mixture consisting completely or partly of polypropylene glycol in which the polypropylene glycol content, based on the polyol mixture, should be no less than 30% by weight and preferably no less than 50% by weight. Mixtures containing more than 70% by weight polypropylene glycol are preferred. A polyol mixture consisting entirely of technical grade propylene glycol is particularly suitable. This variant is preferred inter alia because, on the one hand, polyurethane dispersions prepared from the polyol mixture perform well in performance tests and because, on the other hand, the production process is simplified to the extent that one step—the incorporation of one or more polyols—is saved. Isotactic polypropylene glycol is also suitable.

Polypropylene glycol belongs to a class of compounds well known to the expert, cf. Kirk-Othmer, Encyclopedia of Chemical Technology, 3rd Edition, Vol. 18, John Wiley & Sons, N.Y. 1982, pages 633-645. In theory and even in practice, polypropylene glycols are adducts of propylene oxide started with a molecule containing at least one active hydrogen. Such molecules are alcohols, polyalcohols, amines or even water. Glycerol, propylene glycol, ethylene glycol and trimethylol propane are industrially significant. Suitable amines are, for example ethylene diamine, diethylene triamine and toluene diamine. Other suitable starter molecules and suitable, commercially available polypropylene glycols can also be found in the cited literature reference. Polypropylene glycols having a molecular weight in the range from 200 to 5,000 and, more particularly, in the range from 300 to 3,000 have proved to be particularly favorable. Suitable polypropylene glycols may also contain small quantities, more particularly up to 10 mol. %, based on the educt monomers, of other alkyl oxide units, preferably ethylene oxide, in the polymer chain. These alkyl oxide units may be present in statistical distribution and/or in blocks in the polymer.

One particularly advantageous embodiment of the invention enables completely solventless universal household adhesives to be produced. Completely solventless in the present context means that there are even no residual contents of solvents. This can be ensured by producing the polyurethane dispersions without using solvents. According to the invention, therefore, a solventless polyurethane dispersion prepared without using solvents is preferably used as the universal household adhesive.

In addition, up to 70% by weight, but preferably less, of the polypropylene glycols on which the polyurethane dispersions used in accordance with the invention are based may be replaced by other polyols typically used in preparations of the type in question. A general rule in this regard is that these other polyols must contain at least two reactive hydrogen atoms and should be substantially linear with a molecular weight in the range from 300 to 20,000 and preferably in the range from 400 to 6,000. Preferred other polyols are polyesters, polyacetals, polycarbonates, polyethers, polythioethers, polyamides and/or polyester amides containing on average 2 to at most 4 hydroxyl groups.

In the context of the invention, polycarbonates are understood to be polyesters which, theoretically, can be prepared by esterification of carbonic acid with dihydric or polyhydric alcohols and which bear a hydroxyl group at either end of the chain. The alcohols and, ultimately, the polycarbonate diols preferably have an aliphatic structure. Suitable polyhydric alcohols may be, for example, trihydric, such as glycerol for example. However, dihydric alcohols are preferred, particularly if they contain no less than four and no more than ten carbon atoms. Although cyclic and branched alcohols are suitable, linear alcohols are preferred. The hydroxyl groups may be arranged adjacent, for example in the 1,2-position, or even isolated. OH-terminated diols are preferred. Suitable polycarbonate diols have a molecular weight in the range from 500 to 8,000 and preferably in the range from 800 to 2,500.

Suitable polyethers are, for example, the polymerization products of ethylene oxide, butylene oxide and copolymerization or graft polymerization products thereof and the polyethers obtained by condensation of polyhydric alcohols or mixtures thereof and the polyethers obtained by alkoxylation of polyhydric alcohols, amines, polyamines and aminoalcohols. Other suitable polyethers are the polytetrahydrofurans described in the cited EP 354 471 and ethylene-glycol-terminated polypropylene glycols.

Suitable polyacetals are, for example, the compounds obtainable from glycols, such as diethylene glycol, triethylene glycol, hexanediol and formaldehyde. Suitable polyacetals may also be prepared by polymerization of cyclic acetals.

Among the polythioethers, the condensates of thiodiglycol on its own and/or with other glycols, dicarboxylic acids, formaldehyde, aminocarboxylic acids or aminoalcohols are mentioned in particular. Depending on the co-components, the products are polythioethers, polythio mixed ethers, polythioether esters, polythioether ester amides. Polyhydroxyl compounds such as these may also be used in alkylated form or in admixture with alkylating agents.

The polyesters, polyesteramides and polyamides include the predominantly linear condensates obtained from polybasic, saturated and unsaturated carboxylic acids or their anhydrides and polyhydric, saturated and unsaturated alcohols, aminoalcohols, diamines, polyamines and mixtures thereof and also, for example, polyterephthalates. Polyesters of lactones, for example caprolactone, or of hydroxycarboxylic acids may also be used. The polyesters may contain terminal hydroxyl or carboxyl groups. Relatively high molecular weight polymers or condensates such as, for example, polyethers, polyacetals, polyoxymethylenes may also be (co-)used as alcohol component in their synthesis.

Polyhydroxyl compounds already containing urethane or urea groups and optionally modified natural polyols, such as castor oil, may also be used. Basically, polyhydroxyl compounds containing basic nitrogen atoms such as, for example, polyalkoxylated primary amines or polyesters or polythioethers containing alkyl diethanolamine in co-condensed form may also be used. Polyols obtainable by complete or partial ring opening of epoxidized triglycerides with primary or secondary hydroxyl compounds, for example the reaction product of epoxidized soybean oil with methanol, are also suitable. Copolymers of the polyhydroxyl compounds mentioned are also suitable, as are their analogs preferably terminated by amino or sulfide groups.

According to the invention, the balance to 100% by weight of polyol mixtures consisting partly of polypropylene glycol preferably consists of polytetrahydrofurans, polyethylene glycols, polyacetals, polycarbonates and/or polyesters containing on average 2 to at most 4 OH groups.

The mixture of polyfunctional isocyanates on which the polyurethane dispersions is based consists completely or partly of $\alpha,\alpha,\alpha',\alpha'$-tetramethyl xylene diisocyanate (TMXDI). The meta- and/or para-isomeric form is particularly suitable. Only with a minimum content of TMXDI in the isocyanate mixture is it possible to obtain a polyurethane dispersion with a polypropylene-glycol-based polyol component which gives good adhesion values when used as a universal household adhesive. Accordingly, preferably at least 20% by weight and, better yet, at least 35% by weight of the isocyanate mixture consists of TMXDI. As a general rule, the adhesion values mentioned are better, the higher the content of TMXDI in the isocyanate mixture. Accordingly, mixtures of which half or more, for example two thirds or three quarters, contain TMXDI are preferred.

Suitable additional polyisocyanates, i.e. making up the balance to 100% by weight, are any polyfunctional aromatic and aliphatic isocyanates such as, for example, 1,5-naphthylene diisocyanate, 4,4'-diphenylmethane diisocyanate, 4,4'-diphenyl dimethyl methane diisocyanate, di- and tetraalkyl diphenyl methane diisocyanate, 4,4'-dibenzyl diisocyanate, 1,3-phenylene diisocyanate, 1,4-phenylene diisocyanate, the isomers of tolylene diisocyanate, optionally in admixture, 1-methyl-2,4-diisocyanatocyclohexane, 1,6-diisocyanato-2,2,4-trimethyl hexane, 1,6-diisocyanato-2,4,4-trimethyl hexane, 1-isocyanatomethyl-3-isocyanatomethyl-3-isocyanato-1,5,5-trimethyl cyclohexane, chlorinated and brominated diisocyanates, phosphorus-containing diisocyanates, 4,4'-diisocyanatophenyl perfluoroethane, tetramethoxy butane-1,4-diisocyanate, butane-1,4-diisocyanate, hexane-1,6-diisocyanate, dicyclohexyl methane diisocyanate, cyclohexane-1,4-diisocyanate, ethylene diisocyanate, phthalic acid-bis-isocyanatoethyl ester, also polyisocyanates containing reactive halogen atoms, such as 1-chloromethylphenyl-2,4-diisocyanate, 1-bromomethylphenyl-2,6-diisocyanate, 3,3-bis-chloromethylether-4,4'-diphenyl diisocyanate. Sulfur-containing polyisocyanates are obtained, for example, by reaction of 2 mol hexamethylene diisocyanate with 1 mol thiodiglycol or dihydroxydihexyl sulfide. Other important diisocyanates are trimethyl hexamethylene diisocyanate, 1,4-diisocyanatobutane, 1,2-diisocyanatododecane and dimer fatty acid diisocyanate. Of interest are partly masked polyisocyanates which provide for the formation of self-crosslinking polyurethanes, for example dimeric tolylene diisocyanate, or polyisocyanates partly reacted, for example, with phenols, tertiary butanol, phthalimide, caprolactam.

In one preferred embodiment, the isocyanate component at least partly contains dimer fatty acid isocyanate. Dimer fatty acid is a mixture of predominantly $C_{36}$ dicarboxylic acids which is obtained by thermal or catalytic dimerization of unsaturated $C_{18}$ monocarboxylic acids, such as oleic acid, tall oil fatty acid or linoleic acid. Dimer fatty acids have long been known to the expert and are commercially available. Dimer fatty acid can be reacted to dimer fatty acid isocyanates. Dimer fatty acid diisocyanate is preferred for the purposes of the invention. Technical grade dimer fatty acid, gliisocyanate contains on average at least two and less than three isocyanate groups per molecule dimer fatty acid.

The isocyanates mentioned above may be used individually or in admixture. It is preferred to use—in particular cyclic or branched—aliphatic diisocyanates, more especially isophorone diisocyanate.

The suitable polyfunctional isocyanates preferably contain on average 2 to at most 4 NCO groups. The quantities of polyol mixture and of the mixture of polyfunctional isocyanates are selected so that a certain ratio of NCO-reactive groups to NCO groups is present. The isocyanate component is preferably not present in a substoichiometric quantity but, at the same time, does not exceed two and a half times the percentage of NCO-reactive groups. A ratio of 1:1.05 to 1:2 is particularly favorable. The preferred range—and also the optimal range in regard to the subsequent performance results—is from 1:1.1 to 1:1.6.

The chain extending agents containing reactive hydrogen atoms include the usual saturated and unsaturated glycols, such as ethylene glycol or condensates of ethylene glycol, butane-1,3-diol, butane-1,4-diol, butenediol, propane-1,2-diol, propane-1,3-diol, neopentyl glycol, hexanediol, bis-hydroxymethyl cyclohexane, dioxyethoxy hydroquinone, terephthalic acid-bis-glycol ester, succinic acid di-2-hydroxyethyl amide, succinic acid di-N-methyl-(2-hydroxyethyl)-amide, 1,4-di-(2-hydroxymethylmercapto)-2,3,5,6-tetrachlorobenzene, 2-methylenepropane-1,3-diol, 2-methylpropane-1,3-diol;

aliphatic, cycloaliphatic and aromatic diamines, such as ethylenediamine, hexamethylenediamine, 1,4-cyclohexylenediamine, piperazine, N-methyl propylenediamine, diaminodiphenylsulfone, diaminodiphenyl ether, diaminodiphenyl dimethylmethane, 2,4-diamino-6-phenyl triazine, isophorone diamine, dimer fatty acid diamine; (not included are diamines having unwanted properties which could endanger health, such as for example hydrazine, diaminodiphenyl methane or the isomers of phenylenediamine; also carbohydrazides or hydrazides of dicarboxylic acids)

aminoalcohols, such as ethanolamine, propanolamine, butanolamine, N-methyl ethanolamine, N-methyl isopropanolamine;

aliphatic, cycloaliphatic, aromatic and heterocyclic mono- and diaminocarboxylic acids, such as glycine, 1- and 2-alanine, 6-aminocaproic acid, 4-aminobutyric acid, the isomeric mono- and diaminobenzoic acids, the isomeric mono- and diaminonaphthoic acids; water.

It is emphasized that it is not possible in the context of the invention strictly to distinguish between compounds containing reactive hydrogen atoms with a molecular weight in the range from 300 to 20,000 and the so-called "chain extending agents" because the boundaries between the two classes of compounds are not clearly defined. Compounds which do not consist of several monomer units, but have a molecular weight above 300, such as for example 3,3'-dibromo-4,4'-diaminodiphenyl methane, are classed as chain-extending agents as is pentaethylene glycol although, on the basis of its composition, the latter is actually a polyether diol.

Special chain-extending agents containing at least one basic nitrogen atom are, for example, mono-, bis- or polyalkoxylated aliphatic, cycloaliphatic, aromatic or heterocyclic primary amines, such as N-methyl diethanolamine, N-ethyl diethanolamine, N-propyl diethanolamine, N-isopropyl diethanolamine, N-butyl diethanolamine, N-isobutyl diethanolamine, N-oleyl diethanolamine, N-stearyl diethanolamine, ethoxylated coconut oil fatty amine, N-allyl diethanolamine, N-methyl diisopropanolamine, N-ethyl diisopropanolamine, N-propyl diisopropanolamine, N-butyl diisopropanolamine, C-cyclohexyl diisopropanolamine, N,N-diethoxylaniline, N,N-diethoxyl toluidine, N,N-diethoxyl-1-aminopyridine, N,N'-diethoxyl piperazine, dimethyl-bis-ethoxyl hydrazine,N,N'-bis-(2-hydroxyethyl)-N,N'-diethylhexahydrop-phenylenediamine, N-12-hydroxyethyl piperazine, polyalkoxylated amines, such as propoxylated methyl diethanolamine, also such compounds as N-methyl-N,N-bis-3-aminopropylamine, N-(3-aminopropyl)-N,N'-dimethyl ethylenediamine, N-(3-aminopropyl)-N-methyl ethanolamine, N,N'-bis-(3-aminopropyl)-N,N'-dimethyl ethylenediamine, N,N'-bis-(3-aminopropyl)-piperazine, N-(2 -aminoethyl) -piperazine, N, N'-bisoxyethyl propylenediamine, 2,6-diaminopyridine, diethanolaminoacetamide, diethanolamidopropionamide, N,N-bisoxyethylphenyl thiosemicarbazide, N,N-bis-oxyethylmethyl semicarbazide, p,p'-bis-aminomethyl dibenzyl methylamine, 2,6-diaminopyridine,2-dimethylaminomethyl-2-methylpropane1,3-diol.

Chain-extending agents containing halogen atoms or R-SO$_2$O groups capable of quaternization are, for example, glycerol-1-chlorohydrin, glycerol monotosylate, pentaerythritol-bis-benzenesulfonate, glycerol monomethanesulfonate, adducts of diethanolamine and chloromethylated aromatic isocyanates or aliphatic haloisocyanates, such as N,N-bis-hydroxyethyl-N'-m-chloromethyl phenylurea, N-hydroxyethyl-N'-chlorohexyl urea, glycerol monochloroethyl urethane, bromoacetyl dipropylene triamine, chloroacetic acid diethanolamide. Short-chain isocyanate-reactive diamines and/or dihydroxy compounds are preferred chain-extending agents.

In addition, the polyurethanes on which the polyurethane dispersions used in accordance with the invention are based contain co-condensed carboxylic acids, sulfonic acids or ammonium compounds containing 1 to 2 isocyanate-reactive groups as functional components capable of salt formation in aqueous solution. These functional components may be dihydroxy or even diamino compounds containing an ionizable carboxylic acid, sulfonic acid or ammonium group. These compounds may either be used as such or they may be prepared in situ. To introduce compounds bearing ionizable carboxylic acid groups into the polyurethane, the expert may add to the polyols special dihydroxycarboxylic acids which are only capable of secondary reactions between the carboxyl groups and the isocyanate groups to a limited extent, if at all. A preferred dihydroxycarboxylic acid is, for example, dimethylol propionic acid.

To introduce sulfonic acid groups capable of salt formation, a diaminosulfonic acid may be added to the polyols. Examples are 2,4-diaminobenzenesulfonic acid and also the N-(ω-aminoalkane)-ω'-aminoalkanesulfonic acids described in DE 20 35 732.

To introduce ammonium groups capable of salt formation into the polymer, it is also possible in accordance with DE 15 95 602 cited above to modify the polyurethane prepolymer with an aliphatic and aromatic diamine in such a way that the chains are terminated by primary amino groups which may then be converted into quaternary ammonium compounds or into amine salts with standard alkylating agents.

According to the invention, it is preferred to make the polyurethane prepolymers to be used soluble or redispersible in water by means of carboxylic acid or sulfonic acid groups because polyurethane dispersions containing anionic modifiers such as these can be removed under alkaline conditions, i.e. adhesives of the type in question can be removed from certain substrates, for example from fabrics, under washing conditions.

The polymers are present in salt form in the polyurethane dispersions used in accordance with the invention. In the case of the preferred polymers modified with carboxylic acids or sulfonic acids, alkali metal salts, ammonia or amines, i.e. primary, secondary or tertiary amines, are present as counterions. In the cationically modified products, acid anions, for example chloride, sulfate or the anions of organic carboxylic acids, are present as counterions. The groups capable of salt formation may therefore be completely or partly neutralized by the counterions. An excess of neutralizing agent is also possible.

To obtain substantially clear, i.e. opaque to waterclear, polyurethane dispersions, it is important to maintain a certain ratio between the component capable of salt formation and the other polyuretharie-forming components. Thus, it is best to use the component capable of salt formation in quantities of from 10 to 9,D mol. %, preferably in quantities of from 20 to 80 mol. % anid, more preferably, in quantities of from 30 to 70 mol. %, based on the polyol mixture plus the chain-extending agent optionally present. In addition, the transparency depends; on the degree of neutralization. The expert is able through a few preliminary tests to determine beyond what quantity of modifier capable of ion formation or beyond what quantity of neutralizing agent an adequate degree of transparency is obtained. In general, as little of these components as possible will be used because they can adversely affect the water resistance and resistance to humidity of the adhesive film if used in excessive quantities.

The polyurethane dispersions according to the invention are understood to be two-phase water/polyurethane systems which preferably encompass colloidal systems and sols having particle diameters of up to about 200 nm. These systems are preferably optically opaque to transparent.

The solids content of the adhesive solutions according to the invention may be varied within wide limits. Solids contents of from 20 to 70% by weight and preferably from 30 to 50% by weight have proved effective in practice.

As already mentioned in the discussion of the chain-extending agents suitable for use in accordance with the invention, compounds having health-damaging or health-impairing properties are undesirable, all the more so as the present invention is concerned with a universal adhesive which, presumably, is also going to be used by people whose health is more at risk, such as children, the elderly, the sick, pregnant women, etc. In one particularly preferred embodiment, therefore, not only are physiologically harmful substances, such as hydrazine, not included among the chain-extending agents, the other components of the adhesive are also selected for their physiological harmlessness. The danger to health from free isocyanates or unreacted NCO groups of the polymers or prepolymers, which is often discussed in connection with polyurethane adhesives, does not arise in the case of the present invention because the polyurethanes are dispersed in water and, as any expert knows, isocyanate groups react off with water so that the polyurethane dispersions according to the invention can be guaranteed to contain no reactive NCO groups.

To produce the polyurethanes particularly suitable for the purposes of the invention, the polyols and an excess of diisocyanate are reacted to form an isocyanate-terminated polymer, suitable reaction conditions and reaction times and also temperatures being variable according to the particular isocyanate. The expert knows that the reactivity of the constituents to be reacted necessitates a corresponding equilibrium between reaction velocity and unwanted secondary reactions which lead to discoloration and a reduction in molecular weight. The reaction is typically carried out with stirring over approximately 1 to 6 hours at approximately 50° C. to approximately 120° C.

Suitable production processes for polyurethane dispersions are described, for example, in D. Dieterich, Angew. Makromol. Chem. 98, page 133 (1981) Ullmann, Encyklopädie der technischen Chemie, 4th Edition, Vol. 19, Verlag Chemie, Weinheim/BergstraSe 1974, pages 311-313; Houben-Weyl, Methoden der organischen Chemie, Vol. E 20, Part 1-3, pages 1659-1663 and pages 1671-1681, and in Journal Waterborne Coating, Aug. 1984, pages 2 el Em. The expert so inclined can also find particulars of the relevant patent literature in the secondary literature references cited in these Articles. As known from the already cited EP 354 471, the polyurethane dispersions hitherto suitable as universal household adhesives are preferably produced by the so-called acetone process. Additions of low-boiling solvents, such as acetone for example, are necessary inter alia for reducing the viscosity of the prepolymer and hence to ensure that it can be handled so that dispersion is actually possible. The disadvantage of such production processes, taking into account the need for solventless universal adhesives, is that a technically involved distillation step had to be carried out after the dispersion step to remove at least most of the low-boiling solvent. This involves an additional process step which not only complicates the process, it also adds to the cost of the product, not least because the acetone preferably used cannot be readily returned to the process because anhydrous acetone is preferably used. So far as the expert is concerned, this is inevitably linked inter alia with the question of whether and to what extent a residual solvent content is acceptable because this determines the cost of the process. However, this does conflict with the need for a solventless product. This requirement is actually dictated by consumers in the public debate on solvent residues, for example in household products. Accordingly, there is a need for processes which, on the one hand, lead to the desired products without adversely affecting their desired properties and, on the other hand, can be carried out without any solvent at all, because residual solvent contents can also be avoided in this way.

The hitherto known polyurethane dispersions suitable as universal domestic adhesives cannot be produced by a variant of the solventless dispersion process because even the starting products have an excessive viscosity. On the other hand, known polyurethane dispersions which can be prepared by solventless dispersion processes are not suitable as universal domestic adhesives. Polyurethane dispersions of this type are, for example, those which contain polypropylene glycol as the key constituent of the polyol component. As can be seen from Comparison Example 1 (which corresponds to Comparison Example 1 of EP 354 471) of the Examples of the present application, polyurethane dispersions show inadequate adhesion to substrate surfaces, particularly plastic surfaces, which makes them unsuitable as universal domestic adhesives. In general, it is well known to the expert that polyurethane adhesives based on polypropylene glycol have distinctly poorer adhesion values and tensile shear strengths on almost all surfaces than, for example, polyurethane adhesives based on polyester polyols.

According to the invention, it has been found that a substantially clear and at least substantially solventless aqueous one-component polyurethane dispersion based on the reaction products of a polyol mixture consisting completely or partly of polypropylene glycol, a mixture of polyfunctional isocyanates consisting completely or partly of $\alpha,\alpha,\alpha',\alpha'$-tetramethyl xylene diisocyanate (TMXDI), a functional component capable of salt formation in aqueous solution and optionally a chain-extending agent, can be produced by a solventless process. In other words, the reaction of the reactants mentioned to form the reaction products and the dispersion of the prepolymer phase can be carried out in the absence of inert solvents. To this end, the reactants described above are normally mixed at room temperature. In general, the reaction may be carried out in standard tank reactors. The reaction temperature is in the range from about 70° to 110° C. The reaction mixture may contain effective additions of catalysts for polyurethane reactions. The reactants are normally stirred until the desired NCO value is obtained. The reaction may be carried out by the so-called one-reactor process and also by the so-called two-reactor process. In the first case, the polyurethane prepolymers are dispersed with vigorous stirring while water containing the quantity of base required for neutralization is introduced. On the other hand, however, the prepolymer phase can also be introduced into the aqueous base solution and dispersed therein with vigorous stirring. In both cases, dispersion can take place at elevated temperatures and may optionally be followed by stirring for one to two hours.

The invention described in the foregoing is illustrated by the following Examples.

EXAMPLES

General Production Procedure

The reaction components were mixed at room temperature and stirred in a standard tank reactor at temperatures of 70° to 110° C. until there is no further reduction in the NCO content. Dispersion took place with vigorous stirring while the quantity of base required for neutralization was introduced. The reaction mixture was then stirred for 1 to 2 hours.

EXAMPLE 1

0.5 mol dimethylolpropionic acid
0.1 mol polypropylene glycol, MW 400
0.1 mol polytetrahydrofuran KW 650
0.3 mol polypropylene glycol KW 1000
1.4 mol TMXDI
Solids content: 35%, viscosity: 3,500 mPas
Appearance: opaque-transparent.

EXAMPLE 2

0.55 mol dimethylolpropionic acid
0.15 mol polypropylene glycol, MW 400
0.25 mol polypropylene glycol MW 1,000
0.05 mol polypropylene glycol MW 2,000
0.44 mol IPDI
0.86 mol TMXDI
Solids content: 34.2%, viscosity: 3,000 mpas
Appearance: opaque-transparent.

COMPARISON EXAMPLES 1 AND 2

Acetone Process

The polyols are diluted with acetone or dissolved or dispersed therein. The component capable of ion formation is then added with stirring. Diisocyanate is then added at temperatures of 50° to 70° C. until there is no further reduction in the NCO content. Water containing the bases required for neutralization is then added. Liquid tertiary amines may also be added to the prepolymer shortly before dispersion. After about 30 minutes, water is added. After dispersion for at least 30 minutes, the acetone is distilled off, ultimately under a relatively high vacuum at temperatures of 55° to 60° C.

COMPARISON EXAMPLE 1

| | | |
|---|---|---|
| Glycerol-started polypropylene glycol, OH value 34, MW 3,500 | 100 pbw | 0.09 mol |
| Oleochemical polyol corresponding to DE-PS 37 04 350, OH value 160 | 82 pbw | 0.36 mol |
| Dimethylolpropionic acid | 21.50 pbw | 0.55 mol |
| Acetone | 50 pbw | 2.0 mol |
| Isophorone diisocyanate | 98.05 pbw | 1.45 mol |
| Sodium hydroxide | 6.40 pbw | 0.36 mol |

-continued

| | | |
|---|---|---|
| Water, deionized | 450 pbw | 56.0 mol |

COMPARISON EXAMPLE 2

0.50 mol dimethylolpropionic acid
0.20 mol polypropylene glycol, MW 400
0.30 mol polypropylene glycol MW 1,000
0.6 mol isophorone diisocyanate
0.7 mol hexane diisocyanate
Solids content: 34%, viscosity: 4,000 mPas
Appearance: opaque-transparent Adhesive strength (tensile shear strength, DIN 53 254) in N/mm$^2$

| | Example | | Comparison Example | |
|---|---|---|---|---|
| | 1 | 2 | 1 | 2 |
| Wood*/wood* | 8.4 | 7.8 | 4.5 | 7.0 |
| Wood*/ABS | 3.5 | 3.3 | 1.4 | 1.8 |
| Wood*/Plexiglas | 5.6 | 5.3 | 1.5 | 2.0 |
| Wood*/Alu | 7.5 | 7.6 | 4.9 | 6.5 |

*Beech plywood

The test specimens (5×10 cm$^2$) were bonded after slight roughening and failed after 3 days at a rate of advance of 10 cm/mins.

In the above Examples, MW stands for average molecular weight (approx. values).

We claim:

1. A universal household adhesive composition comprising a substantially clear and solvent-free, aqueous, one-component polyurethane dispersion containing the reaction products of
   (a) a polyol mixture comprising polypropylene glycol,
   (b) a mixture of polyfunctional isocyanates comprising α, α, α$^1$, α$^1$-tetramethyl xylene diisocyanate,
   (c) a functional component capable of salt formation in aqueous solution, and
   (d) optionally, a chain-extending agent.

2. A universal household adhesive composition as in claim 1 wherein said polypropylene glycol has a molecular weight of from about 200 to about 5,000.

3. A universal household adhesive composition as in claim 1 wherein said polyol mixture contains at least about 30% by weight of polypropylene glycol.

4. A universal household adhesive composition as in claim 3 wherein said polyol mixture further contains polytetrahydrofuran, polyethylene glycol, polyacetal, polycarbonate and polyester containing on average 2 to 4 OH groups.

5. A universal household adhesive composition as in claim 1 wherein said mixture of polyfunctional isocyanates contains at least about 20% by weight of said α, α, α$^1$, α$^1$-tetramethyl xylene diisocyanate.

6. A universal household adhesive composition as in claim 5 wherein said mixture of polyfunctional isocyanates contains an aliphatic isocyanate containing on average 2 to 4 NCO groups.

7. A universal household adhesive composition as in claim 1 wherein said polyol mixture and said mixture of polyfunctional isocyanates are present in a ration of NCO-reactive groups to NCO groups of from about 1:1 to about 1:2.5.

8. A universal household adhesive composition as in claim 1 wherein said functional component capable of salt formation in aqueous solution is selected from the group consisting of a carboxylic acid, sulfonic acid, and ammonium compound containing 1 to 2 isocyanate-reactive groups.

9. A universal household adhesive composition as in claim 8 wherein said functional component is in the form of an alkali metal salt, ammonium salt, or salt of a primary, secondary or tertiary amine.

10. A universal household adhesive composition as in claim 8 wherein said carboxylic acid comprises dimethylol propionic acid.

11. A universal household adhesive composition as in claim 1 wherein said functional component capable of salt formation is present in an amount of about 10 to about 90 mol. %, based on said polyol mixture plus any content of chain-extending agent.

12. A universal household adhesive composition as in claim 1 containing a chain-extending agent selected from the group consisting of an isocyanate-reactive diamine and a dihydroxy compound.

13. A universal household adhesive composition as in claim 1 wherein the clarity of said composition is controlled by the quantity present of said functional component capable of salt formation.

14. A universal household adhesive composition as in claim 1 wherein the clarity of said composition is controlled by the quantity of neutralizing agent added for said functional component capable of salt formation.

15. The process of producing a substantially clear and solvent-free, aqueous, one-component polyurethane dispersion comprising reacting (a) a polyol mixture comprising polypropylene glycol,
(b) a mixture of polyfunctional isocyanates comprising $\alpha, \alpha, \alpha^1, \alpha^1$-tetramethyl xylene diisocyanate,
(c) a functional component capable of salt formation in aqueous solution, and
(d) optionally, a chain-extending agent, in the absence of an inert solvent, and dispersing the reaction products in the absence of an inert solvent.

16. A process as in claim 15 wherein the reactants are mixed at room temperature, the mixture is stirred at a temperature of about 70° C. to about 110° C. until the desired NCO value has been obtained, and the reaction mixture is dispersed in water.

17. A process as in claim 16 wherein said water contains a quantity of base material sufficient to neutralize the polyurethane prepolymers.

* * * * *